United States Patent [19]

Bray

[11] Patent Number: 4,765,333
[45] Date of Patent: Aug. 23, 1988

[54] SURGICAL METHODS AND APPARATUS FOR BONE REMOVAL

[76] Inventor: Robert S. Bray, 411 Pinata Pl., Fullerton, Calif. 92635

[21] Appl. No.: 620,062

[22] Filed: Jun. 13, 1984

Related U.S. Application Data

[62] Division of Ser. No. 498,093, May 25, 1983, Pat. No. 4,596,243.

[51] Int. Cl.⁴ .............................................. A61F 17/32
[52] U.S. Cl. ............................ 128/305.1; 128/92 VD
[58] Field of Search ............. 128/92 R, 92 E, 92 EB, 128/310, 305.1

[56] References Cited

U.S. PATENT DOCUMENTS

| | | | |
|---|---|---|---|
| 2,326,908 | 8/1943 | Williams | 255/72 |
| 3,382,743 | 5/1965 | Trevathan | 77/69 |
| 4,111,208 | 9/1978 | Leuenberger | 128/305.1 |
| 4,274,769 | 6/1981 | Multakh | |
| 4,362,161 | 12/1982 | Reimels et al. | 128/310 |

Primary Examiner—C. Fred Rosenbaum
Assistant Examiner—Mark O. Polutta
Attorney, Agent, or Firm—Price, Gess & Ubell

[57] ABSTRACT

Surgical methods and apparatus for craniotomy flap removal and other delicate bone removal procedures utilizing a core drill driven in such a manner as to give a recognizable indication of near-penetration of the bone surface addressed, thereby preventing injury to highly delicate underlying tissues.

5 Claims, 1 Drawing Sheet

SURGICAL METHODS AND APPARATUS FOR BONE REMOVAL

This is a division of application Ser. No. 498,093, filed May 25, 1983 now U.S. Pat. No. 4,596,243 issued June 24, 1986.

BACKGROUND OF THE DISCLOSURE

The subject invention relates to surgical procedures and apparatus for the removal of bone. The subject invention is particularly directed to highly delicate procedures involved in areas such as brain and spinal surgery. The methods and apparatus according to the invention considerably reduce the risk of paralysis and other serious damage presently attendant to such procedures.

One procedure where the subject invention finds particular use is in the area of craniotomy flap removal, a procedure for opening up the skull used in brain surgery. The state of the art flap removal procedure involves use of a fluted drill to drill a series of "burr" holes in the cranium at spaced-apart locations around the section of cranium to be removed. A cutting tool is then inserted to join up the holes. Such a procedure may take from thirty to forty-five minutes and results in considerable loss of bone.

In the current approach to craniotomy flap removal, there is a considerable danger of penetration of the dura, a membrane lying between the brain and skull. There is also the risk of penetration of the brain itself. Such damage may result from the considerable plunging pressure which must be applied to drills currently in use and the tendency of such drills to "pull through" once they have penetrated completely through the skull.

In an attempt to reduce potential injury to the dura or brain, prior art drills have used a clutching mechanism to disengage the drill upon encountering soft tissue. However, at this point some damage may already have occurred, and the plunging pressure applied may still propel the drill into the subcranial matter.

Depth guages have also been suggested to indicate depth of penetration into the skull. However, such a device does not eliminate the plunging propensity of the drill. In addition, the varying thickness of the skull is an obstacle to accurate guaging of penetration. This variance may range from 0.080 to 0.30 inches thick.

Another highly delicate surgical procedure where the invention finds use is a procedure known as anterior surgical fusion. In this procedure, sections of bone must be removed from adjacent vertebra. Access to the vertebrae is gained by entry through the neck, which complicates the drilling approach. Slippage of the drill in such a procedure is an ever-present risk and has caused complete and permanent paralysis of patients. The present invention makes this process much safer by greatly reducing, if not entirely eliminating, the risk of accidental slippage or plunging.

SUMMARY OF THE INVENTION

It is therefore an object of the invention to provide an improved surgical apparatus and procedure for bone removal.

It is a further object of the invention to lower the risk of serious injury attendant to present methods and apparatus for bone removal in areas where drilling error can result in serious physical injury.

Other objects and advantages will be apparent from the ensuing description taken with the knowledge of those skilled in the art.

The objects and advantages of the invention are achieved by use of a core drill, such as typically used in the glass cutting art, driven with a high speed, low amplitude oscillation about a central axis. It has been discovered that when driven in this manner, the core drill exhibits a selective penetration property —its cutting rate slows dramatically at a depth near to complete penetration.

It has been discovered that in craniotomy flap removal, for example, such a core drill will circumscribe a desired section of the skull and stop just short of penetration through to the dura at a depth which permits the circumscribed bone plug or flap to be easily pried out. As the core drill nears penetration of the bone, the bone becomes thin and flexible, and the core drill exhibits the unforeseen property that it practically stops cutting. This property may be visually sensed by observing the decrease in flow of cutting debris as the rate of cutting slows. The procedure may be completed in one to five minutes, depending on the width of the drill, and leaves a circular bone flap which may be replaced, resulting in a much faster and cosmetically more desirable healing.

The drill performs with similar advantage in anterior surgical fusion and permits a replacement bone plug to be cut from the illium to match the plug removed from the vertebrae area. The replacement plug may be cut more rapidly since a less delicate area is involved.

BRIEF DESCRIPTION OF THE DRAWINGS

The just described invention will now be described in more detail in conjunction with the drawings of which.

DETAILED DESCRIPTION OF THE PREFERRED EMBODIMENT

Figure 1:
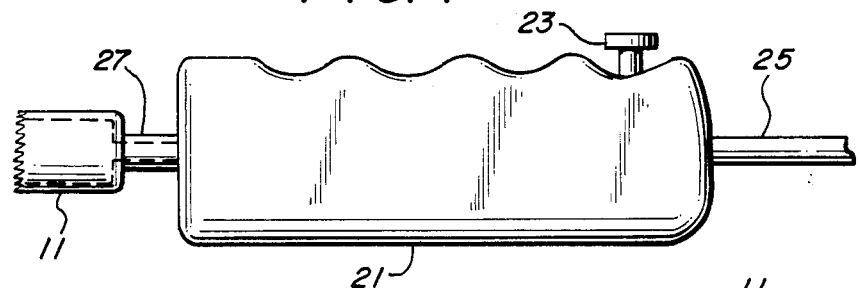
FIG. 1 is a perspective view of the apparatus of the preferred embodiment of the invention.
Figure 2:
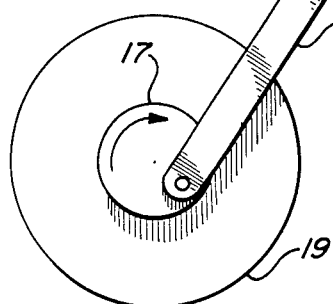
FIG. 2 is a view of the apparatus of the subject invention viewed from the cutting face shown out of scale for clarity of illustration.

The apparatus of the preferred embodiment is shown in FIGS. 1 and 2. It includes a diamond or other abrasive-coated core drill 11. This core drill is preferably a 60 grit although other grits (30–200) may find application. The shaft of the core drill 11 is connected to an arm 13. The arm 13 is pivotally connected to a second arm 15 which is pivotally mounted to an eccentric point 18 on a cam 17. The cam 17 is driven by an air or electric motor 19 or other suitable drive means. The motor 19 is preferably autoclavable.

In operation, the cam 13 and arms 15, 17 convert the rotating motion of the drive shaft of motor 19 into a high speed, low amplitude rotational oscillation imparted to the drill 11. The speed is preferably in the range of 15,000 to 25,000 oscillations per minute (o.p.m.), 20,000 o.p.m. having been found to be a preferred choice. The speed is high in the sense that tool durability will be sacrificed at higher speeds. At lower speeds the cutting rate is decreased. Oscillations in the general range of 1,000 to 50,000 (o.p.m.) might be used in various circumstances.

Referring to FIG. 1, a housing 21 contains the motor 19 and drive apparatus. The core drill 11 extends out of the housing 19. The housing 21 also carries an activation switch 23 and a hose or tube 25 carrying power (e.g., air or electricity) and water for irrigation. This water is conducted to the cutting area through a channel 27 in the core drill 11.

The degree of peripheral travel imparted to the drill is approximately seven degrees for a ½ inch core drill. It is desirable to limit total peripheral linear deplacement to about 0.020 to 0.2 inch with oscillations of about 0.040 to 0.060 inch being preferred in sensitive areas. Core drills of a diameter out to approximately 2½ inches and as small as desired can be used, eliminating in many instances the necessity to drill more than one hole to complete a surgical procedure.

The procedure according to the invention is to apply the core drill to the skull or other hard bone area and to activate the tool. Light pressure on the order of one to 1½ pounds is required, compared to approximately 3 pounds required by typical prior art. The drill penetrates rapidly compared to the prior art, leaving only a powder-like residue. The drilling operation is carried out with a flood of water to cool and carry away debris from the cut area. The drill ceases cutting as the bone section becomes thin enough to be flexible. Cutting debris ceases to flow at this point, providing an indication to the operator that penetration is near.

The operator then ceases drilling and pries out the circular bone plug with an appropriate tool. Because the drill removes so little material it has been found that the plug may be used to close the opening if desired.

Figure 3:
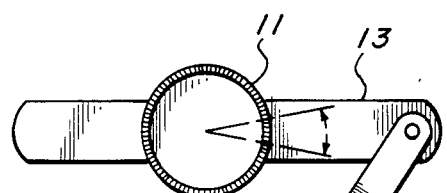
FIG. 3 is a side view of a human skull illustrating exemplary cranial flaps.
Figure 3:
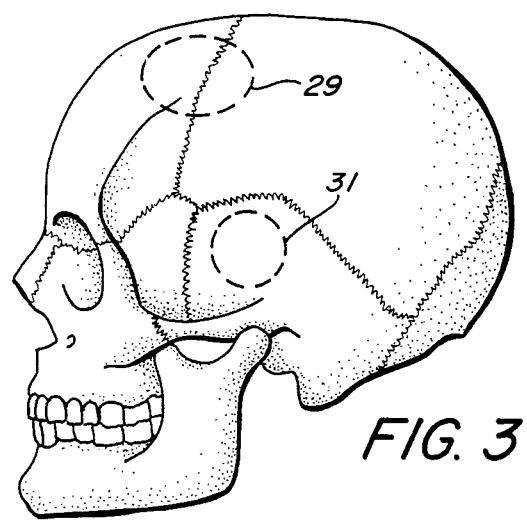

FIG. 3 shows typical plugs 29, 31 removed in craniotomy flap removal. In the preferred procedure for craniotomy flap removal, after the bone plug 29, 31 is removed, surgical procedures within the skull are performed. To close the skull, the plug 29, 31 is replaced and sutured into place. The reuse of the plug provides an improvement in healing time because of the very fine cut made and provides a cosmetically more satisfactory healing. The core drill 11 itself provides long term durability.

It may be noted that even if the drill of the invention is allowed to totally penetrate the skull, no damage to the underlying tissues will occur because it will not penetrate soft material. Evensurgical gloves are not damaged by contacting the activated drill.

With respect to craniotomy flap removal, the drill of the preferred embodiment also may be rocked or angulated to accomplish cutting contoured surfaces and nonuniform thickness areas. Such use, of course, requires the skill of a surgeon familiar with the contours and varying thicknesses involved.

A 1½ to 2 inch outside diameter may be used for removal of small craniotomy flaps in such procedures as aneurism surgery, posteria fossa, craniotomy and CT guided stereotactic open resection. A 2 to 3 inch outside diameter is used to remove a standard craniotomy flap for general neurosurgical application including such procedures as tumor resection and emergency hematoma. Drills of ⅜ to ⅞ inch outside diameter may be used to create standard burr holes in the skull.

Figure 4:
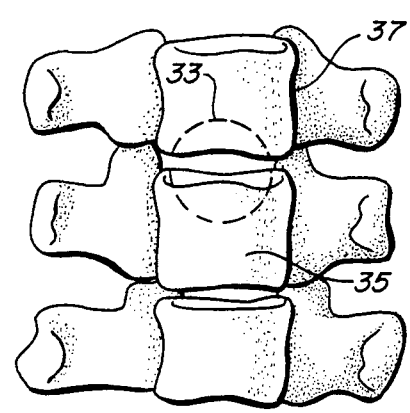
FIG. 4 illustrates a vertebral bone area.
Figure 5:
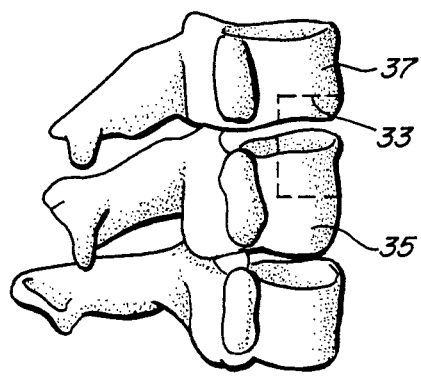
FIG. 5 is another view of the vertebral area of FIG. 5.

The procedure for anterior cervical fusion is illustrated in FIGS. 4 and 5. A bone plug 33 is removed from two adjacent vertebra 35, 37 using the core drill 11. In this procedure it is very difficult to judge the depth of penetration of a conventional drill toward the spinal chord. However, the core drill 11 slows when it reaches the thick casing surrounding the spinal chord, enabling safe operation. In addition, the cut is so clean that a bone plug may be cut from the illium with another appropriately sized core drill to fit the opening 33. Prior art techniques using rotary curved saws resulted in ragged edges and numerous bone chips. It may be noted that when cutting a replacement plug from the illum, the cutting rate of the core drill may be increased over that used in sensitive areas by using a coarser grit and increased pressure.

It will be apparent from the foregoing that the invention is applicable in numerous circumstances. Therefore, it is to be understood that, within the scope of the appended claims, the invention may be practiced other than as specifically described herein.

What is claimed is:

1. Surgical apparatus for use in removing bone from an area of a given thickness comprising:
   motor drive means providing a drive shaft rotating at a constant rotational speed; and
   means driven by said drive means for cutting a substantially circular bone plug and for substantially slowing cutting at a depth just short of the thickness of the bone area to which said apparatus is applied.

2. The surgical apparatus of claim 1 wherein said means driven by said drive means comprises:
   a cylinder having an abrasive substance bonded about the rim of one end; and
   means connected at the opposite end of said cylinder and driven by said drive shaft for moving said cylinder about its axis in a low amplitude, high frequency alternating motion.

3. The apparatus of claim 2 wherein the arc of travel of said alternating motion is on the order of 0.020 to 0.2 inches in length.

4. The apparatus of claim 2 wherein said frequency is in the range of 15,000 to 25,000 oscillations per minute.

5. The apparatus of claim 3 wherein said frequency is in the range of 15,000 to 25,000 oscillations per minute.

* * * * *